United States Patent
Bhatia et al.

(10) Patent No.: US 7,674,812 B2
(45) Date of Patent: Mar. 9, 2010

(54) TRIPLE ANTI-IRRITANT COMPOSITION

(75) Inventors: Kuljit S. Bhatia, Chandler, AZ (US); Bhiku G. Patel, Chandler, AZ (US); Eugene H. Gans, Westport, CT (US)

(73) Assignee: Medicis Pharmaceutical Corp., Scottsdale, AZ (US)

( * ) Notice: Subject to any disclaimer, the term of this patent is extended or adjusted under 35 U.S.C. 154(b) by 0 days.

(21) Appl. No.: 12/082,027

(22) Filed: Apr. 7, 2008

(65) Prior Publication Data
US 2008/0213409 A1 Sep. 4, 2008

Related U.S. Application Data

(62) Division of application No. 10/884,146, filed on Jul. 2, 2004.

(51) Int. Cl.
A61K 31/4166 (2006.01)
A61K 31/045 (2006.01)

(52) U.S. Cl. .................. 514/389; 514/729; 514/828; 514/844; 424/401

(58) Field of Classification Search .......... 424/744, 424/401; 514/729, 390, 349, 828, 844
See application file for complete search history.

(56) References Cited

U.S. PATENT DOCUMENTS

| | | | |
|---|---|---|---|
| 3,634,264 A | 1/1972 | Pence et al. | |
| 4,388,301 A | 6/1983 | Klein et al. | |
| 4,545,990 A | 10/1985 | Le Foyer de Costil et al. | |
| 4,587,123 A | 5/1986 | Price et al. | |
| 4,735,935 A | 4/1988 | McAnalley | |
| 4,752,472 A | 6/1988 | Kligman | |
| 4,803,228 A | 2/1989 | Jacquet et al. | |
| 4,891,228 A | 1/1990 | Thaman et al. | |
| 4,906,617 A | 3/1990 | Jacquet et al. | |
| 4,917,891 A | 4/1990 | Kaufmann et al. | |
| 4,960,772 A | 10/1990 | Sebag et al. | |
| 5,019,567 A | 5/1991 | Philippe et al. | |
| 5,254,109 A | 10/1993 | Smith et al. | |
| 5,368,581 A | 11/1994 | Smith et al. | |
| 5,470,884 A | 11/1995 | Corless et al. | |
| 5,562,642 A | 10/1996 | Smith et al. | |
| 5,632,996 A | 5/1997 | Ramirez et al. | |
| 5,648,389 A | 7/1997 | Gans et al. | |
| 5,660,839 A | 8/1997 | Allec et al. | |
| 5,690,946 A | 11/1997 | Koulbanis et al. | |
| 5,756,107 A | 5/1998 | Hahn et al. | |
| 5,756,119 A | 5/1998 | Deckner et al. | |
| 5,767,098 A | 6/1998 | Klein et al. | |
| 5,804,203 A | 9/1998 | Hahn et al. | |
| 5,821,237 A | 10/1998 | Bissett et al. | |
| 5,874,074 A | 2/1999 | Smith et al. | |
| 5,874,093 A | 2/1999 | Eliaz et al. | |
| 5,951,991 A | 9/1999 | Wagner et al. | |
| 5,958,436 A | 9/1999 | Hahn et al. | |
| 5,997,885 A | 12/1999 | Koulbanis et al. | |
| 6,001,380 A | 12/1999 | Smith et al. | |
| 6,017,549 A | 1/2000 | Knight et al. | |
| 6,113,921 A | 9/2000 | Friedman et al. | |
| 6,153,208 A | 11/2000 | McAtee et al. | |
| 6,183,766 B1 | 2/2001 | Sine et al. | |
| 6,338,855 B1 | 1/2002 | Albacarys et al. | |
| 6,413,536 B1 | 7/2002 | Gibson et al. | |
| 6,429,231 B1 | 8/2002 | Bhagwat et al. | |
| 6,455,076 B1 | 9/2002 | Hahn et al. | |
| 6,462,025 B2 | 10/2002 | Vishnupad | |
| 6,469,227 B1 | 10/2002 | Cooke et al. | |
| 6,861,397 B2 | 3/2005 | Seitz et al. | |
| 6,977,081 B1 | 12/2005 | Rood | |
| 2002/0086039 A1 | 7/2002 | Lee et al. | |
| 2002/0164381 A1 | 11/2002 | Shacknai et al. | |
| 2003/0031727 A1 | 2/2003 | Hahn et al. | |
| 2005/0025817 A1 | 2/2005 | Bhatia et al. | |
| 2005/0232978 A1 | 10/2005 | Patel et al. | |

FOREIGN PATENT DOCUMENTS

| | | |
|---|---|---|
| EP | 0576287 | 12/1993 |
| JP | 03-002124 | 1/1991 |
| WO | WO 82/04393 | 12/1982 |
| WO | WO 98/04241 | 2/1998 |
| WO | WO 99/24003 | 5/1999 |

OTHER PUBLICATIONS

Harry, R.G., "Harry's Cosmeticology", pp. 558-561, 6th edition (1973).

(Continued)

*Primary Examiner*—Shengjun Wang
*Assistant Examiner*—Sahar Javanmard
(74) *Attorney, Agent, or Firm*—William J. McNichol; Reed Smith LLP

(57) ABSTRACT

The present invention relates to a composition comprising two or more anti-irritants, each having at least about 7.2% oxygen content. In a separate embodiment, the composition may be defined to include a skin conditioning agent, a skin protectant agent, and an anti-irritant agent, each having an oxygen content of at least about 7.2%. The invention further comprises methods of treating and preventing skin conditions by applying the composition to the skin, and then optionally washing the skin.

13 Claims, No Drawings

OTHER PUBLICATIONS

Bonnar, et al., "The Demodex Mite Population in Rosacea", Journal of the American Academy of Dermatology, vol. 28, No. 3, pp. 443-448, Mar. 1993.

Diaz-Perez et al., "Demodex mites in Rosacea" and "Reply", Journal of the American Academy of Dermatology, vol. 30, No. 5, Part 1, pp. 812-813, May 1994.

"Dermatology in General Medicine", 5$^{th}$ edition, CD-ROM, Chapter 74, (1999).

Lin et al., "Sulfur Revisited", Journal of the American Academy of Dermatology, vol. 18, No. 3, pp. 553-558, Mar. 1998.

Maibach, et al., "Sulfur Revisited" and "Reply", Journal of the American Academy of Dermatology, vol. 23, No. 1, pp. 154-156, Jul. 1990.

The Merck Manual, Seventeenth Edition (1999), pp. 811-814.

Marks, "Histopathology of Rosacea", Arch. Derm., vol. 100, pp. 683-691, Dec. 1969.

Database WPI Section Ch. Week 1986 Derwent Publications Ltd. London, GB; AN 1986-040399 XP002245540 & RO 87 009 A (Intr Prod Cosmetice Farmec) May 30, 1985 (abstract).

Physician's Desk Reference, 2004, 58$^{th}$ edition, published Nov. 2003, Thomas Healthcare, pp. 1906-1907.

Merck Index pp. 697-698, 1288-1289 (1983).

Ayres et al. "Demodectic Eruptions (Demodicidosis) in the Human," Arch. Derm., vol. 83, May 1961, pp. 816-827.

Milks, Howard Jay, "Sulfur Compounds" Practical Veterinary Pharmacology, Materia Medica and Therapeutics, 1949, Sixth Edition, pp. 552-560.

Alexander Jo'D., "Hair follicle mites in men," In Arthropods and Human Skin, Berlin: Spreinger-Verlag, 1984.

Schewach-Miller et al., "Granulomatous rosacea," Journal of the American Academy of Dermatology, Jun. 1988, vol. 18, No. 6, pp. 1363-1362.

Dominey et al., "Papulondular demodicidosis associated with acquired immunodeficiency syndrome," Journal of the American Academy of Dermatology, Feb. 1989, vol. 20, pp. 197-201.

Ecker, et al., "Demodex Granuloma," Arch Dermatol; Mar. 1979, vol. 115, pp. 343-344.

Physicians Desk Reference, 57 Edition, Montvale, NJ (2003) Plexion pp. 1926-1927.

Waller, T. "Aloe Vera in Personal Care Products," *Cosmetic & Toiletries*, (Aug. 1992).

Moroni P., "Aloe in Cosmetic Formulations," *Cosmetic Technology* (Sep. 1982).

"Aloe Vera Gel," Handbook of Non-Prescription Drugs, American Pharmaceutical Ass'n., Washington, D.C., p. 707 (1996).

"Allantoin," Handbook of Non-Prescription Drugs, American Pharmaceutical Ass'n., Washington, D.C., pp. 548 and 640 (1996).

Jappe, U., "Pathological Mechanisms of Acne with Special Emphasis on Propionibacterium acnes and related Therapy," *Acta Derm Venereol*, ;83 pp. 241-248 (2003).

Basta-Juzbasic, A., "Demodex Folliculorum in Development of Dermatitis Rosaceiformis Steroidica and Rosacea-Related Diseases," *Clinics in Dermatology*, 20 pp. 135-140 (2002).

"α-Bisabolol" *Merck Index*, Merck & Co., Twelve Edition, p. 208-209 (1996).

"Allantoin" *Merck Index*, Merck & Co., Twelve Edition, p. 48 (1996).

"Mannose" *Merck Index*, Merck & Co., Twelve Edition, p. 979 (1996).

Manna, S, "Determination of the Position of the *O*-Acetyl Group in a β-(1 → 4)-Mannan (Acemannan) from *Aloe barbardensis* Miller," *Carbohydrate Research*, 241, pp. 317-319 (1993).

CTFA Cosmetic Ingredient Handbook, pp. 64-65, 78-85 (1988).

International Cosmetic Ingredient Dictionary and Handbook, pp. 65, 69-74, 185, 2929-2938 (2002).

Steinberg, D., "U.S. Regulations Update: FDA Issues Final Monograph for Skin Protectants," *Cosmetics & Toiletries*, 118(8) pp. 20-28 (Aug. 2003).

Martindale, 32d Edition, pp. 11 (1999).

TRIPLE ANTI-IRRITANT COMPOSITION

RELATED APPLICATIONS

This application is a divisional application under 35 USC § 121 of U.S. application Ser. No. 10/884,146, filed Jul. 2, 2004 which is still pending.

FIELD OF THE INVENTION

The present invention relates to a stable composition which includes two or more anti-irritants which each contain at least about 7.2% oxygen content. In a separate embodiment, the composition of the invention may be described as including a skin conditioning agent, a skin protectant agent and an anti-irritant agent, each of which contains at least about 7.2% oxygen content. The compositions of the present invention can be used alone or in conjunction with other skin treatment agents or pharmaceutically active ingredients. The present invention also relates to a method of treating and/or preventing various skin conditions and is especially useful for individuals with sensitive skin.

BACKGROUND OF THE INVENTION

A large population of people suffer from various inflammatory skin conditions including acne, rosacea, atopic dermatitis, various seborrheas, eczema, psoriasis, various mite infestations, various scabies infestations, other inflammatory skin conditions, and the clinical symptoms thereof, just to name a few examples. These skin disorders are accompanied by increased irritation and may also cause an increase in the presence of microorganisms. In this specification, irritation is defined as a condition of redness, itching, burning, pain and/or discomfort of the skin, and may include inflammation, soreness, or irritability of the skin. These clinical symptoms can be painful, bothersome, and have a negative effect on the quality of life of the patient. Thus, treatment is often necessary. Each skin condition may affect a different layer or layers of the skin. For example, mild acne involves inflammation of the upper part of the pilosebaceous follicle while mite infestation involves inflammation which may be due to the excretions of mites in one or more of the stratum corneum, epidermal tissue, and the pilosebaceous follicle. When treating these conditions, it is important for the appropriate agents to reach the appropriate layer of skin in order for the treatment to be effective. A skin treatment composition that can reach various layers of the skin, thereby effectively treating skin problems, is needed.

Another problem associated with various skin disorders is the negative side effects associated with the pharmaceutically active ingredients. Treatment with pharmaceutically active ingredients may aggravate and inflame the skin causing dryness, flaking, cracking and peeling. These side effects are especially problematic in individuals with sensitive skin. These negative side effects may have an effect on patient compliance. Individuals who suffer severe side effects may fail to follow the prescribed treatment schedule or may even discontinue treatment altogether. Thus, a composition is needed to help treat and lessen the effects associated with pharmaceutically active ingredients.

SUMMARY OF THE INVENTION

The present invention relates to a combination of two or more, preferably three or more, anti-irritants, each having at least about 7.2% oxygen content. This composition is hereinafter referred to as Embodiment A.

Oxygen content is defined as the ratio of (the molecular weight of oxygen atoms available for van der Waals associations) to (the molecular weight of the compound as a whole). Where an ingredient is a mixture of more than one compound, the oxygen content is calculated on the basis of active compounds in the mixture (i.e., the ratio of (the molecular weight of oxygen atoms available for van der Waals associations in the active compounds) to (the molecular weight of the active compounds)). For example, the oxygen content of aloe vera gel is based on the amount of oxygen in acetylated mannose (acemannan), its active compound. Without limitation, oxygens in alcohols, hydroxyl groups, aldehydic groups, oxime groups, ester groups, and some keto and carboxyl groups have available electrons in their outer shell that can be shared with other atoms. We refer to these molecules as electron rich oxygen molecules. Oxygens in epoxy groups, ether groups, and some substituted carboxyl, amide and ester groups, without limitation, have less or little of this ability as will be recognized by one of ordinary skill in the art. Van der Waals associations allow the electron rich oxygen molecules to associate with electron poor atoms and molecules (such as hydrogen, amide, and other groups). This can produce enhanced penetration in some cases and it can also produce enhanced binding at therapeutic sites.

The present invention requires both hydrophilic and lipophilic groups which provide the required hydrophilicity and lipophilicity that are needed to treat various inflammatory skin conditions. A range of oxygen content may be suitable for the present invention provided that the compound possesses both hydrophilic and lipophilic properties which enable the compound to reach various tissue layers. Aliphatic and benzeneoid structures, for example, without limitation, tend to be more lipophilic while polar oxygen containing chemical groups, such as, without limitation, hydroxyl, keto, oxime and ester groups, tend to be more hydrophilic. The hydrophilicity of these groups is due to the ability of the oxygen atoms to form van der Waals associations with water molecules.

Preferably, the anti-irritants of the present invention are used as skin treatment agents. A skin treatment agent is defined as an agent that has a dermatological, cosmetic, or pharmaceutical effect on the skin. Anti-irritants are well known in the art. One of ordinary skill in the art would understand, appreciate and recognize agents that are considered to be anti-irritants. Preferred anti-irritants include but are not limited to aloe vera gel, alpha bisabolol, allantoin, sorbitol, urea, lactic acid and salts, glucose derivatives, zinc acetate, zinc carbonate, zinc oxide, potassium gluconate, dimethicone, glycerin, petrolatum, lanolin, peramides, uric acid and salts, N-acetyl cysteine, and hydrocortisone.

One embodiment of the invention includes aloe vera gel, allantoin, and alpha bisabolol. Aloe vera gel, allantoin and alpha-bisabolol vary in their oxygen content. Aloe vera gel has an oxygen content of greater than about 50%, compared to about 30.4% for allantoin, and about 7.2% for alpha-bisabolol.

Aloe vera gel is obtained from the leaves of *Aloe barbadensis*. It has a moisturizing and revitalizing effect. Aloe vera penetrates the skin thereby providing moisture directly to the tissues. It also acts to moisturize the skin by forming a protective barrier on the skin which prevents the loss of moisture through evaporation. Aloe vera gel is also known to have anti-inflammatory and antimicrobial effects and to enhance wound healing. The gel consists of a mixture of several types of polysaccharides including mannan, glucomannan, an acidic galactan, an arabinan and/or a glucogalactomannan. It is believed, without being limited to this belief, that the active chemical substance in aloe is a polymer of acetylated mannose monomers. The amount of aloe vera used in a product varies depending on its intended use as would be recognized by one of ordinary skill in the art.

In prior art embodiments, a product that remains in contact with the skin can have aloe vera concentrations up to 10% and products that remain in contact with the skin for very short periods of time may contain greater than 60% aloe vera. However, according to the present invention, about 0.05% to about 5.0% aloe vera gel may be used. Preferably, about 0.1% to about 1.0% aloe vera gel is used. More preferably, about 0.1% to about 0.5% aloe vera gel is used. Most preferably, about 0.1% aloe vera gel is used. It will be apparent to one of ordinary skill in the art that any form of aloe may be used in the present invention if suitable for topical use. Unless otherwise specified, all percentages listed in this specification are weight percentages.

Allantoin acts to soften keratin and is used as a skin protectant agent and in this way as an anti-irritant. The most common use of allantoin is for the prevention and treatment of dry and chapped skin and lips. According to the present invention, about 0.05% to about 5.0% allantoin may be used. Preferably, the present invention includes about 0.1% to about 1.0% allantoin. Most preferably, the invention includes about 0.1% allantoin.

Alpha-bisabolol is known for its anti-irritant effects. Alpha-bisabolol is available in both natural and synthetic forms. Both forms may be used in the present invention. The active form of alpha-bisabolol is the (−) isomer. The natural form is derived from the oils of the tropical shrub candeia and from the oils of the chamomile plant. These natural oils can be used to prepare about 95% or greater pure (−) alpha-bisabolol. The synthetic form, however, contains about 42% of the active isomer. Thus, while either form may be used, the natural form is preferred for use in the present invention. Up to about 2% or higher of synthetic or natural alpha-bisabolol may be used in the present invention. In certain embodiments, up to about 2% of the natural form of alpha-bisabolol, preferably about 0.1% to about 0.5%, more preferably about 0.1% to about 0.25%, and most preferably about 0.1% is used.

Without being limited thereto, it is believed that the presence of both hydrophilic (or polar oxygen-bearing) chemical groups and lipophilic chemical groups in each component of the present invention is responsible for facilitating the anti-irritant and other skin treatment effects provided by the present invention. Without limitation, it is believed that the lipophilic and hydrophilic properties of the anti-irritants of the present invention enable the components to reach the desired tissue layer and thereby effectively treat dermatological problems such as, but not limited to, acne, rosacea, atopic dermatitis, various seborrheas, eczema, psoriasis, various mite infestations, various scabies infestations, other inflammatory skin conditions, and clinical symptoms thereof. The present invention may also be useful in enhancing the absorption of active ingredients into various layers of the skin.

A separate embodiment comprises at least one skin conditioning agent, at least one skin protectant agent, and at least one anti-irritant agent, all of which have at least about 7.2% oxygen content. This composition is hereinafter referred to as Embodiment B. A skin conditioning agent means an agent used to enhance the appearance of dry or damaged skin and which adheres to the skin to reduce flaking and restore suppleness. Skin conditioning agents are well known in the art. One of ordinary skill in the art would understand, appreciate and recognize agents that are considered to be skin conditioning agents. An extensive list of skin conditioning agents can be found in the International Cosmetic Ingredient Dictionary and Handbook published by the Cosmetic, Toiletry, and Fragrance Association, Inc., under the listing "Skin-Conditioning Agents," (herein incorporated by reference). Preferred skin conditioning agents include, but are not limited to, aloe vera gel, fatty alcohols, esters, amides, glycols, selective alcohols, polymers, and the like.

A skin protectant agent is an agent which protects injured or exposed skin or mucous membrane surfaces from harmful or annoying stimuli and includes, but is not limited to, allantoin, calamine, cocoa butter, dimethicone, glycerin, kaolin, petrolatum, shark liver oil, silicates, silicas, protectant clays, zinc acetate, zinc carbonate, and zinc oxide. Skin protectant agent are well known in the art. One of ordinary skill in the art would understand, appreciate and recognize agents that are considered to be skin protectant agents. An extensive list of skin protectant agents can be found in the International Cosmetic Ingredient Dictionary and Handbook published by the Cosmetic, Toiletry, and Fragrance Association, Inc., under the listing "Skin Protectants," (herein incorporated by reference).

An anti-irritant agent is an agent used to reduce skin irritation and inflammation and includes but is not limited to alpha-bisabolol. Anti-irritant agents are well known in the art. One of ordinary skill in the art would understand, appreciate and recognize agents that are considered to be anti-irritant agents. Again, it is believed, without being limited to the mechanism, that the presence of both hydrophilic and lipophilic groups in the skin conditioning agent, skin protectant agent and anti-irritant agent provides the hydrophilicity and lipophilicity that are needed to reach various tissue layers, thereby effectively treating dermatological problems.

The present invention, including but not limited to Embodiments A or B, may also be useful in enhancing or facilitating the absorption of active ingredients into various layers of the skin.

In addition, the invention relates to a method of treating and preventing skin irritation by applying the present compositions described in the specification including but not limited to Embodiment A or Embodiment B to the skin. Treating is defined to include the minimization, reduction or lessening of skin irritation. Prevention is defined to include the complete or partial avoidance of skin irritation. Preferably, Embodiment A or Embodiment B, without being limited thereto, may be used to treat or prevent skin inflammation, promote skin healing, control of the growth of microorganisms on the skin, and treat or prevent skin discomfort or pain. In a separate embodiment, the method includes applying a composition containing aloe vera gel, allantoin, and alpha-bisabolol to the skin surface. The skin disorders that can be treated or prevented by use of the compositions described in the specification, for example, without limitation, Embodiment A and Embodiment B, include but are not limited to acne, rosacea, atopic dermatitis, various seborrheas, eczema, psoriasis, various mite infestations, various scabies infestations, other inflammatory skin conditions, and clinical symptoms thereof.

Another embodiment of the invention relates to a method of treating and preventing skin irritation by washing the skin with the compositions described in the specification, for example, without limitation, Embodiment A and Embodiment B. In a separate embodiment, the method includes washing the skin with a composition containing aloe vera gel, allantoin, and alpha-bisabolol.

DETAILED DESCRIPTION OF THE SPECIFIC EMBODIMENTS

In the present invention, two or more anti-irritants, preferably three or more, each having at least about 7.2% oxygen content, are combined to treat and prevent skin irritation. More specifically, the present invention involves a composition containing aloe vera gel, allantoin, and alpha-bisabolol. This novel combination acts to treat skin conditions and also functions in combination with other skin treatment agents to lessen the side effects associated with those other skin treatment agents.

In a separate embodiment, the composition may be defined to include at least one skin conditioning agent, at least one skin protectant agent, and at least one anti-irritant agent, each agent having at least 7.2% oxygen content. In a preferred embodiment, the skin conditioning agent is aloe vera gel, the skin protectant agent is allantoin, and the anti-irritant agent is alpha-bisabolol. These components have oxygen contents ranging from about 7.2% to greater than about 50%.

In certain embodiments, a composition comprising two or more, preferably three or more, anti-irritants, each having at least about 7.2% oxygen content, may be combined with other ingredients as would be recognized by one of ordinary skill in the art, such as, without limitation, solvents, viscosity adjuster compositions, cleansers, propellants, emollients, emulsifiers, moisturizers, odor modifiers, preservatives, fragrances, vehicles, pharmaceutical active ingredients, immunomodulator or immunosuppressant agents, antiparasitic agents, keratinization modulators, depigmenting agents, antihistamines, antimicrobial agents, antifungal agents, anti-inflammatory agents, analgesics, and antioxidants.

Antimicrobial agents may include any antimicrobial agents useful in dermatological compositions. Antimicrobial agents include, without limitation, benzoyl peroxide, povidone iodine, hexachlorphene, chlorhexidine, mupirocin, gentimycin, neomycin, bacitracin, polymixin, erythromycin, clindamycin, metronidazole, clarithromycin, silver sulfadiazine, dapsone, zinc pyrithione, cephalosporin, thymol, mafenide acetate, nitrofurazone, generators of nitric oxide benzyl alcohol, sulfamethoxazole, sulfasalazine, sulfasoxazole, acetylsulfasoxazole and combinations thereof. Antimicrobial agents are well known in the art. One of ordinary skill in the art would understand, appreciate and recognize agents that are considered to be antimicrobial agents. An extensive list of antimicrobial agents can be found in the International Cosmetic Ingredient Dictionary and Handbook published by the Cosmetic, Toiletry, and Fragrance Association, Inc., under the listing "Antimicrobial Agents," (herein incorporated by reference).

Antifungal agents may include any antifungal agents useful in dermatological compositions. Examples of antifungal agents include, without limitation, nystatin, ciclopirox and ciclopirox olamine, griseofulvin, itraconazole, fluconazole, ketoconazole, terbinafine, econazole, benzyl alcohol, undecylenic acid and salts thereof, benzyl benzoate and combinations thereof. Antifungal agents are well known in the art. One of ordinary skill in the art would understand, appreciate and recognize agents that are considered to be antifungal agents. An extensive list of antifungal agents can be found in the International Cosmetic Ingredient Dictionary and Handbook published by the Cosmetic, Toiletry, and Fragrance Association, Inc., Linder the listing "Antifungal Agents," (herein incorporated by reference).

Antiparasitic agents may include any antiparasitic agents useful in dermatological compositions. Antiparasitic agents include, without limitation, malathion, pediculosides, scabicides, ivermectin, perrnethrin, pyrethrin, carbamyl, imiquimod, thiabendazol, and combinations thereof. Antiparasitic agents are well known in the art. One of ordinary skill in the art would understand, appreciate and recognize agents that are considered to be antiparasitic agents.

Keratinization modulators may include any keratinization modulators useful in dermatological compositions. Keratinization modulators include, without limitation, retinol, retinoic acid, retinaldehyde, retinal, retinyl esters, tazarotene and other retinoids, alpha and beta hydroxy acids salicylic acid, resorcinol, retinal esters and combinations thereof. Keratinization modulators are well known in the art. One of ordinary skill in the art would understand, appreciate and recognize agents that are considered to be keratinization modulators.

In addition, anti-inflammatory agents and/or immunomodulators or immunosuppressants may be added as part of the invention to enhance their anti-irritant effect. Suitable anti-inflammatory agents may include any anti-inflammatory agents useful in dermatological compositions. Suitable anti-inflammatory agents include, without limitation, aldometasone, betamethasone, esters of betamethasone, desonide, clobetasole propionate, clocortolone pivilate, triamcinilone acetonide, mometosone furoate, prednicarbate, fluocinonide, fluocinolone acetonide, hydrocortisone and combinations thereof. Anti-inflammatory agents are well known in the art. One of ordinary skill in the art would understand, appreciate and recognize agents that are considered to be anti-inflammatory agents.

Suitable immunomodulators or immunosuppressants may include any immunomodulators or immunosuppressants useful in dermatological compositions. Suitable immunomodulators or immunosuppressants include, without limitation, cylclosporine, imiquimod, flurouracil, podophilox, podophyllin, and combinations thereof. Preferred immunomodulators or immunosuppressants consist of cylclosporine, imiquimod, and flurouracil. Immunomodulators and immunosuppressants are well known in the art. One of ordinary skill in the art would understand, appreciate and recognize agents that are considered to be immunomodulators or immunosuppressants.

In other embodiments, a composition comprising aloe vera gel, allantoin, and alpha-bisabolol may be combined with other ingredients as would be recognized by one of ordinary skill in the art, such as, without limitation, solvents, viscosity adjuster compositions, cleansers, propellants, emollients, emulsifiers, moisturizers, antioxidants, odor modifiers, preservatives, fragrances, vehicles, pharmaceutically active ingredients, immunomodulator or immunosuppressant agents, antiparasitic agents, keratinization modulators, depigmenting agents, antihistamines, antimicrobial agents, antifungal agents, anti-inflammatory agents, analgesics, and antioxidants.

In certain embodiments, a composition comprising one or more skin conditioning agents, one or more skin protectant agents, and one or more anti-irritant agents, all having an oxygen content of at least about 7.2%, may be combined with other ingredients as would be recognized by one of ordinary skill in the art, such as, without limitation, solvents, viscosity adjuster compositions, cleansers, propellants, emollients, emulsifiers, moisturizers, antioxidants, odor modifiers, preservatives, fragrances, vehicles, pharmaceutical active ingredients, immunomodulator or immunosuppressant agents, antiparasitic agents, keratinization modulators, depigmenting agents, antihistamines, antimicrobial agents, antifungal agents, anti-inflammatory agents, analgesics, and antioxidants.

The following table sets forth an embodiment of the present invention:

TABLE 1

| Ingredient | % w/w* |
|---|---|
| Aloe Vera Gel Decolorized, 1X | 0.10% |
| Allantoin | 0.10% |
| Alpha-bisabolol Natural | 0.10% |

*% w/w is percent of the total composition.

In one embodiment, the present invention relates to the novel combination of at least two of the three ingredients described above in Table 1 and preferably all three ingredients. Each possesses a quality beneficial to the treatment and/or prevention of various skin conditions. The combination of at least two of the three ingredients acts to treat and/or prevent a variety of clinical symptoms and can be used to treat and/or prevent one or multiple skin conditions. It will be obvious to one of skill in the art that other ingredients may be added without departing from the spirit of the invention. For example, solvents, viscosity adjuster compositions, cleansers, propellants, emollients, emulsifiers, moisturizers, antioxidants, odor modifiers, preservatives, fragrances, vehicles, pharmaceutically active ingredients, immunomodulator or immunosuppressant agents, antiparasitic agents, keratinization modulators, depigmenting agents, antihistamines, antimicrobial agents, antifungal agents, anti-inflammatory agents, analgesics, antioxidants and other components that do not interfere with the stated functions of the above-mentioned ingredients may be added within the scope of the present invention.

For example, another embodiment of the present invention is set forth below:

TABLE 2

| Ingredient | % w/w |
|---|---|
| Sodium Sulfacetamide | 11.24 |
| Sulfur | 5.00 |
| Sodium Methyl Oleyltaurate (Tauranol MS) | 9.15 |
| Sodium Cocoyl Isethionate (Tauranol I-78C) | 6.50 |
| Disodium Laureth Sulfosuccinate (and) Sodium Lauryl Sulfoacetate (Stepan-Mild LSB) | 4.50 |
| Disodium Oleamido MEA Sulfosuccinate (Mackanate OM) | 3.85 |
| Glycerine | 2.00 |
| Sorbitan Monooleate NF (Crill 4 NF) | 2.00 |
| Glyceryl Stearate and PEG-100 Stearate (Arlacel 165) | 2.00 |
| Stearyl Alcohol NF (Crodacol S-95 NF) | 1.50 |
| Propylene Glycol (and) PEG-55 Propylene Glycol Oleate (Antil 141 Liquid) | 1.35 |
| Cetyl Alcohol NF (Crodacol C-95 NF) | 1.00 |
| Disodium EDTA | 0.20 |
| Methylparaben NF | 0.15 |
| PEG-150 Pentaerythrityl Tetrastearate (Crothix) | 0.15 |
| Butylated Hydroxytoluene NF (BHT) | 0.15 |
| Sodium Thiosulfate | 0.15 |
| Aloe Vera Gel Decolorized, 1X | 0.10 |
| Allantoin | 0.10 |
| Alpha-bisabolol Natural | 0.10 |
| Fragrance | 0.10 |
| Propylparaben NF | 0.05 |
| Purified Water | 48.66 |

Embodiment A, B, and other embodiments of the present invention may be used to treat and/or prevent a variety of clinical symptoms and can be used to treat and/or prevent multiple skin conditions. In particular, the embodiments may be used to treat or prevent skin inflammation, promote skin healing, control of the growth of microorganisms on the skin, and treat or prevent skin discomfort or pain. More particularly, the present invention can be used to treat or prevent acne, rosacea, atopic dermatitis, various seborrheas, eczema, psoriasis, various mite infestations, various scabies infestations, other inflammatory skin conditions, and clinical symptoms thereof.

In order to be effective, the anti-irritants found in the present invention must reach the appropriate layer of skin. Without being limited to the mechanism, it is believed that these ingredients are useful in treating a variety of skin conditions due to the presence of both hydrophilic and lipophilic groups in their chemical structures.

For example, mild acne involves inflammation of the upper part of the pilosebaceous follicle, known as the infundibulum, which is lipophilic. Severe acne, on the other hand, also involves the presence of inflammatory sebum in the dermis which is primarily hydrophilic. Rosacea may involve inflammation in the hydrophilic stratum corneum and epidermal tissue and in the lipophilic pilosebaceous infundibulum. Thus, the ability of the skin treatment agents to reach both the lipophilic and hydrophilic layers of the skin is essential for effective prevention and treatment and in reducing clinical symptoms.

Another embodiment containing aloe vera gel, allantoin, and alpha-bisabolol demonstrates the range of hydrophilic and lipophilic groups that are present. More than half of the molecular weight of aloe vera gel is attributed to the oxygen content, compared to 30.4% oxygen content for allantoin and 7.2% oxygen content for alpha-bisabolol. Thus, this combination of ingredients provides both the hydrophilic and lipophilic groups that are needed to treat inflammatory problems that are present in both hydrophilic and lipophilic layers of the skin, such as acne and rosacea. In addition, the present invention may also be used to treat one or more skin conditions simultaneously. It is believed, without being limited to the mechanism, that the ability of the ingredients to reach both hydrophilic and lipophilic tissues allows a physician to treat a patient with more than one disorder with one composition. This may increase patient compliance and help to reduce patient costs.

Another aspect of the present invention includes adding pharmaceutically active ingredients. The present invention can be used to treat and prevent the side effects associated with the pharmaceutically active ingredients. Common side effects include but are not limited to drying, scaling, irritation, erythema, itching, burning, and sensitization reactions. The invention including one or more pharmaceutically active ingredients is especially useful for patients with sensitive skin where the side effects may have a deleterious effect on patient compliance.

For example, the present invention can include, without limitation, sulfur, sodium sulfacetamide, antimicrobial agents, antifungal agents, antiparasitic agents, antiacne agents, anti-rosacea agents, agents for treating and preventing various eczemas and inflammations, anti-psoriasis agents, and keratinization modulators.

Another embodiment of the present invention is directed to a method of treating and preventing skin irritation by applying to the skin an effective amount of one of the compositions described in this specification. Preferably, Embodiment A, Embodiment B, or another embodiment may be used to treat or prevent skin inflammation, promote skin healing, control of the growth of microorganisms on the skin, and treat or prevent skin discomfort or pain. In one embodiment, Embodiment A, Embodiment B, or another embodiment of the composition will be applied to the skin and will remain on the skin for an extended period of time.

In another embodiment of the invention, the skin surface is washed with an effective amount of Embodiment A, Embodiment B, or another embodiment. The composition will only remain in contact with the skin for various short periods of time and will then be washed away from the skin surface. For example, without limitation, Embodiment A, Embodiment B, or another embodiment of the composition may remain on the skin up to about thirty seconds or preferably from about thirty seconds to about thirty minutes. Depending on the type of skin condition treated and the severity of the condition, one of ordinary skill in the art will appreciate the benefits of short contact therapy for certain disorders, and specific active ingredients. Also, the frequency of application and/or washing will be apparent to one of skill in the art.

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A method of treating skin irritation comprising applying a composition to skin consisting essentially of sulfur, sodium sulfacetamide, a first anti-irritant which is alpha-bisabolol, a second anti-irritant which is allantoin, and a third anti-irritant which is aloe vera gel, wherein each anti-irritant has at least about 7.2% oxygen content.

2. The method of claim 1 wherein the alpha-bisabolol is present in an amount from about 0.1% to about 2.0%.

3. The method of claim 2 wherein the alpha-bisabolol is present in an amount from about 0.1% to about 0.5%.

4. The method of claim 3 wherein the alpha-bisabolol is present in an amount from about 0.1% to about 0.25%.

5. The method of claim 1 wherein the second anti-irritant has at least about 30.4% oxygen content.

6. The method of claim 1 wherein the allantoin is present in an amount from about 0.05% to about 5.0%.

7. The method of claim 6 wherein the allantoin is present in an amount from about 0.1% to about 1.0%.

8. The method of claim 1 wherein the third anti-irritant has at least about 50% oxygen content.

9. The method of claim 1 wherein the aloe vera gel is present in an amount from about 0.05% to about 5.0%.

10. The method of claim 9 wherein the aloe vera gel is present in an amount from about 0.1% to about 1.0%.

11. The method of claim 10 wherein the aloe vera gel is present in an amount from about 0.1% to about 0.5%.

12. The method of claim 1 further comprising washing the skin after the application.

13. The method of claim 1 wherein the skin irritation comprises one or more of the group consisting of acne, rosacea, atopic dermatitis, various seborrheas, eczema, psoriasis, various mite infestations, and various scabies infestations.

* * * * *